(12) United States Patent
Adams et al.

(10) Patent No.: US 8,389,723 B1
(45) Date of Patent: Mar. 5, 2013

(54) DEUTERATED BENZENE SULFONAMIDE THIAZOLE COMPOUNDS

(75) Inventors: Jerry Leroy Adams, Collegeville, PA (US); Dashyant Dhanak, Collegeville, PA (US); Dirk A. Heerding, Collegeville, PA (US); Calvin O. Manning, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/558,427

(22) Filed: Jul. 26, 2012

Related U.S. Application Data

(60) Provisional application No. 61/526,716, filed on Aug. 24, 2011.

(51) Int. Cl.
*C07D 417/04* (2006.01)
*C07D 403/04* (2006.01)
(52) U.S. Cl. ........................................ 544/333
(58) Field of Classification Search .................. 544/331
See application file for complete search history.

(56) References Cited

U.S. PATENT DOCUMENTS

| | | | |
|---|---|---|---|
| 6,603,008 B1 * | 8/2003 | Ando et al. ................. | 546/269.7 |
| 2009/0298815 A1 * | 12/2009 | Adams et al. .............. | 514/227.8 |

* cited by examiner

*Primary Examiner* — Noble Jarrell
*Assistant Examiner* — Laura Daniel
(74) *Attorney, Agent, or Firm* — J. Scott Young

(57) ABSTRACT

Deuterated forms of N-{3-[5-(2-Amino-4-pyrimidinyl)-2-(1,1-dimethylethyl)-1,3-thiazol-4-yl]-2-fluorophenyl}-2,6-difluorobenzenesulfonamide and pharmaceutical compositions containing the same.

1 Claim, No Drawings

DEUTERATED BENZENE SULFONAMIDE THIAZOLE COMPOUNDS

CROSS-REFERENCE TO RELATED APPLICATION

The instant application claims priority to U.S. Provisional Patent Application Ser. No. 61/526,716, filed 24 Aug. 2011 which is incorporated herein in its entirety.

FIELD OF THE INVENTION

The present invention relates to deuterated forms of the kinase inhibiting compound N-{3-[5-(2-Amino-4-pyrimidinyl)-2-(1,1-dimethylethyl)-1,3-thiazol-4-yl]-2-fluorophenyl}-2,6-difluorobenzenesulfonamide, pharmaceutical formulations comprising the same, and their use in therapy and processes for preparing the same.

BACKGROUND OF THE INVENTION

The compound N-{3-[5-(2-Amino-4-pyrimidinyl)-2-(1,1-dimethylethyl)-1,3-thiazol-4-yl]-2-fluorophenyl}-2,6-difluorobenzenesulfonamide and a genus of compounds encompassing that compound have been found to be active inhibitors of particular kinases, particularly the B-Raf kinase. Such usefulness is disclosed in, for instance, international patent publication WO2009/137391. The WO'391 publication specifically discloses N-{3-[5-(2-Amino-4-pyrimidinyl)-2-(1,1-dimethylethyl)-1,3-thiazol-4-yl]-2-fluorophenyl}-2,6-difluorobenzenesulfonamide compound, crystalline forms thereof, and salts thereof.

It is desired to provide additional forms of N-{3-[5-(2-Amino-4-pyrimidinyl)-2-(1,1-dimethylethyl)-1,3-thiazol-4-yl]-2-fluorophenyl}-2,6-difluorobenzenesulfonamide having properties suitable for use in pharmaceutical formulations.

DESCRIPTION OF THE INVENTION

The present inventors have now discovered deuterated compounds which are BRAF inhibitors. Such compounds may be useful in the treatment of conditions mediated by BRAF inhibition.

According to a general embodiment of the invention, there is provided a compound of Formula (I):

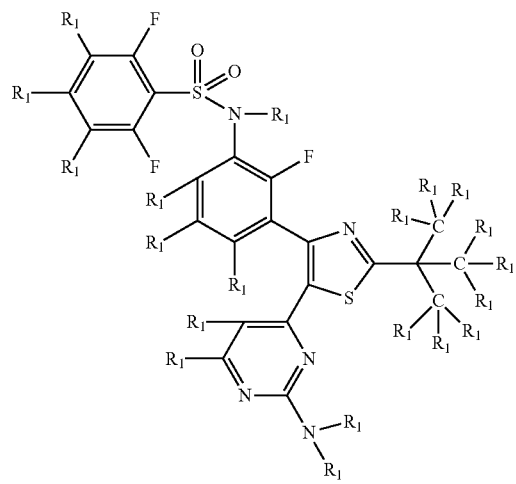

(I)

wherein:
$R_1$ is independently selected from -D or —H, wherein "-D" represents a deuterium atom and "—H" represents a hydrogen atom, and wherein at least one $R_1$ substituent is a deuterium atom;
or a pharmaceutically acceptable salt thereof.

In a particular embodiment of the present invention, there is provided a compound of Formula (Ia):

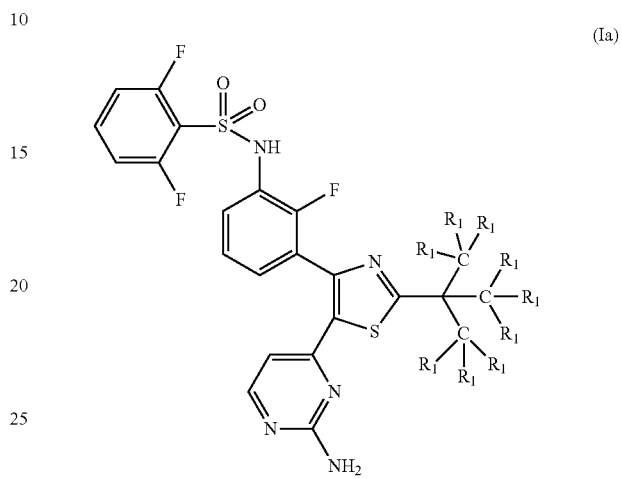

(Ia)

wherein:
$R_1$ is independently selected from -D or —H, wherein "-D" represents a deuterium atom and "—H" represents a hydrogen atom, and wherein at least one $R_1$ substituent is a deuterium atom;
or a pharmaceutically acceptable salt thereof.

In a particular embodiment of the present invention, there is provided a compound of Formula (Ib):

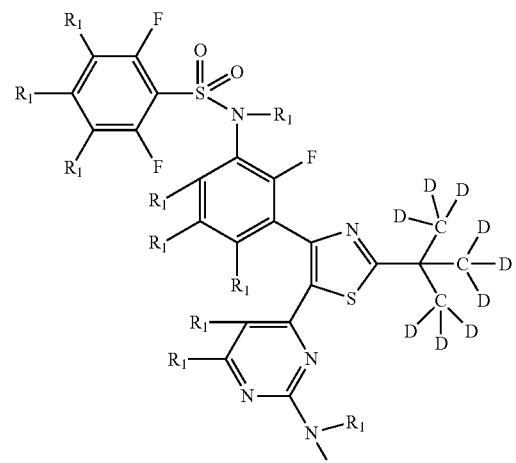

(Ib)

wherein:
$R_1$ is independently selected from -D or —H, wherein "-D" represents a deuterium atom and "—H" represents a hydrogen atom, and wherein at least one $R_1$ substituent is a deuterium atom;
or a pharmaceutically acceptable salt thereof.

In a particular embodiment of the present invention, there is provided a compound of Formula (Ic):

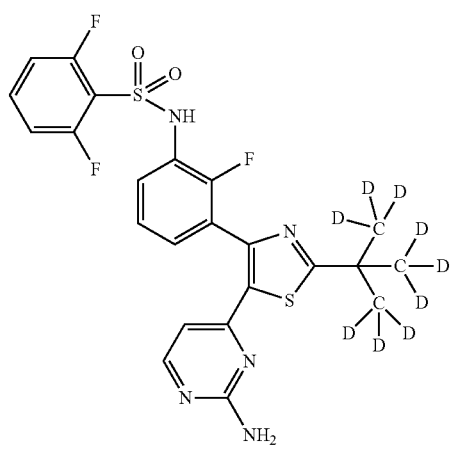
(Ic)
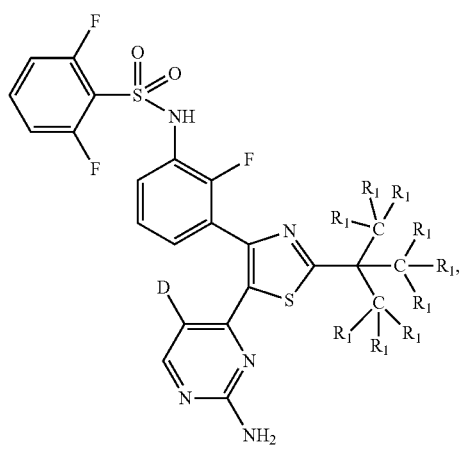
wherein any atom not designated as deuterium is present at its natural isotopic abundance.
In a particular embodiment of the invention, there is provided a compound selected from the formulas
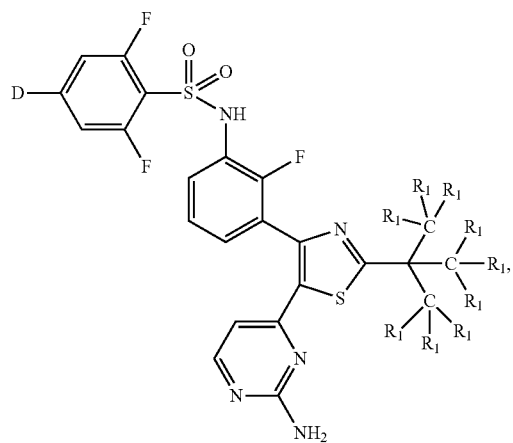
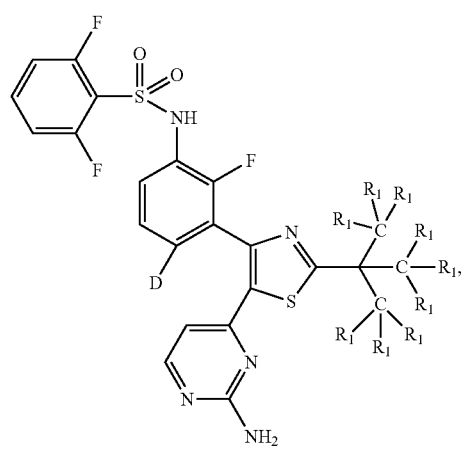
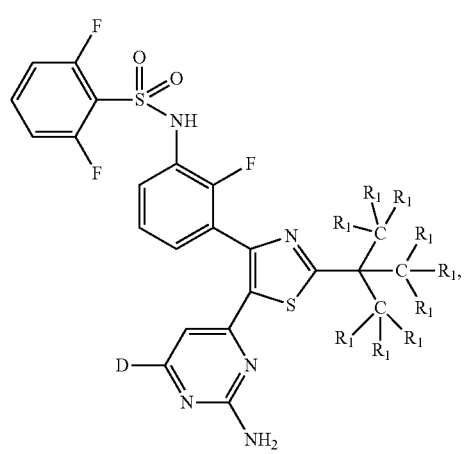
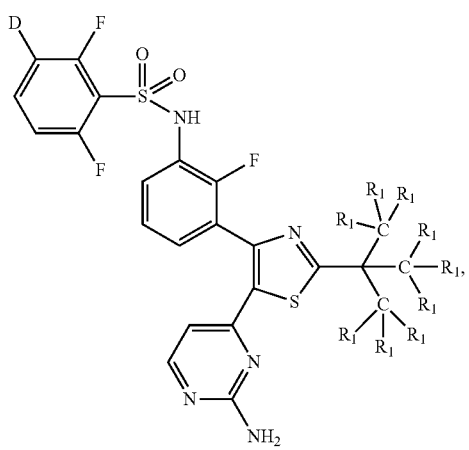

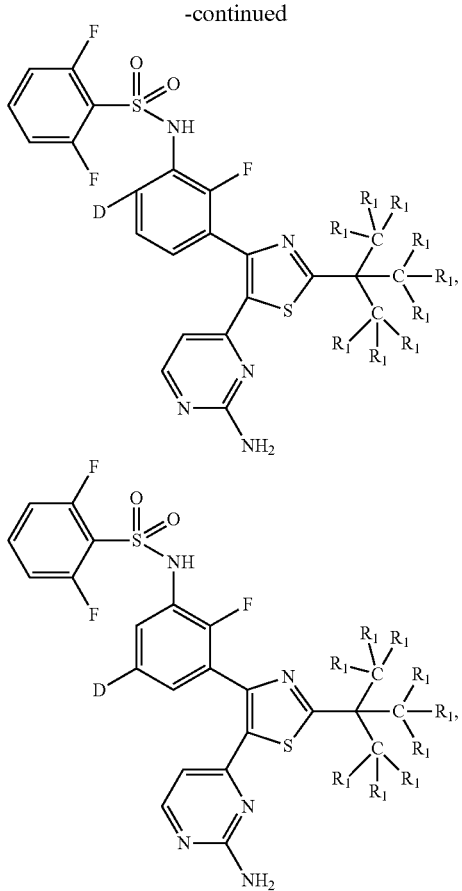

wherein:

R₁ is independently selected from -D or —H, wherein "-D" represents a deuterium atom and "—H" represents a hydrogen atom, and wherein at least one R₁ substituent is a deuterium atom;

or a pharmaceutically acceptable salt thereof.

As used herein and known in the art, the term "H" refers to a hydrogen atom. Hydrogen (H, $^1$H), is a stable isotope of hydrogen that contains 1 proton having an atomic number of 1 and a mass number of 1. Also, unless otherwise stated when a particular $R^1$ is substituted with —H it is understood to have hydrogen and deuterium at their natural abundance isotopic composition.

It will be apparent to one skilled in the art that due to the natural abundance of deuterium (0.015%) that compounds of formula (I) will be present at some minor level in compounds previously made wherein all positions were dictated to be 'hydrogens'. However the low percentage of deuterium isotopes in mono deuterium containing analogues and even lower (0.015%×0.015%) for dual deuterium containing analogues and henceforth higher deuteron analogues is insignificant to the pharmacological effect of previously described drug molecules.

In the present invention, the compounds of formula (I) (wherein "formula (I)" is used to include, in the alternative, the formulas (Ia), (Ib), and (Ic) throughout the description below) are substantially enriched in deuterium to levels of 50% at the indicated positions. In many cases the preferred level of deuterium incorporation at the indicated position is above 75%, 90%, 95% or 98% and approaching limits of quantitation for determining hydrogen ($^1$H) content. It will also be understood that compounds with multiple deuterium atoms incorporated will have isotopic mixtures dependent on the level of incorporation at each position.

Accordingly, in one embodiment, the level of deuterium incorporation in each $R^1$ group of the compound of formula (I) indicated as substituted with deuterium is at least 50%. In another embodiment, the level of deuterium incorporation in each $R^1$ group of the compound of formula (I) indicated as substituted with deuterium is at least 75%. In still another embodiment, the level of deuterium incorporation in each $R^1$ group of the compound of formula (I) indicated as substituted with deuterium is at least 90%. In a further embodiment, the level of deuterium incorporation in each $R^1$ group in the compound of formula (I) indicated as substituted with deuterium is at least 95%. In another embodiment, the level of deuterium incorporation in each $R^1$ group of the compound of formula (I) indicated as substituted with deuterium is at least 98%. In a further embodiment, the level of deuterium incorporation in each $R^1$ group of the compound of formula (I) indicated as substituted with deuterium approaches 100% and is limited by the limits of quantitation for detecting hydrogen content.

In one embodiment, the level of deuterium incorporation in each $R^1$ group of the compound of formula (I) indicated as substituted with deuterium is at least 20%. In another embodiment, the level of deuterium incorporation in each $R^1$ group of the compound of formula (I) indicated as substituted with deuterium is at least 25%. In still another embodiment, the level of deuterium incorporation in each $R^1$ group of the compound of formula (I) indicated as substituted with deuterium is at least 30%. In a further embodiment, the level of deuterium incorporation in each $R^1$ group in the compound of formula (I) indicated as substituted with deuterium is at least 35%. In another embodiment, the level of deuterium incorporation in each $R^1$ group of the compound of formula (I) indicated as substituted with deuterium is at least 40%. In a further embodiment, the level of deuterium incorporation in each $R^1$ group of the compound of formula (I) indicated as substituted with deuterium is at least 45%.

In one embodiment, the level of deuterium incorporation in each $R^1$ group of the compound of formula (I) indicated as substituted with deuterium is greater than 0.015%. In another embodiment, the level of deuterium incorporation in each $R^1$ group of the compound of formula (I) indicated as substituted with deuterium is at least 1%. In still another embodiment, the level of deuterium incorporation in each $R^1$ group of the compound of formula (I) indicated as substituted with deuterium is at least 3%. In a further embodiment, the level of deuterium incorporation in each $R^1$ group in the compound of formula (I) indicated as substituted with deuterium is at least 5%. In another embodiment, the level of deuterium incorporation in each $R^1$ group of the compound of formula (I) indicated as substituted with deuterium is at least 10%. In a further embodiment, the level of deuterium incorporation in each $R^1$ group of the compound of formula (I) indicated as substituted with deuterium is at least 15%.

It will be understood by those skilled in the art that the level of deuterium incorporation in each $R^1$ group indicated as substituted with deuterium may be the same or similar or may be different with the only limitation being the recited lower limit. For instance when the lower limit is at least 50% incorporation of deuterium, each deuterium substituted for hydrogen may be incorporated at any value of 50% or greater. That is, one deuterium substituted $R^1$ may have 60% deuterium incorporation whereas another deuterium substituted $R^1$ may have 80% deuterium incorporation and so on for other deuterium substituted $R^1$ groups.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compounds of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

The present invention includes deuterated N-{3-[5-(2-Amino-4-pyrimidinyl)-2-(1,1-dimethylethyl)-1,3-thiazol-4-yl]-2-fluorophenyl}-2,6-difluorobenzenesulfonamide both in substantially pure form and in admixture with other forms of N-{3-[5-(2-Amino-4-pyrimidinyl)-2-(1,1-dimethylethyl)-1,3-thiazol-4-yl]-2-fluorophenyl}-2,6-difluorobenzenesulfonamide, including admixtures of salts, particularly the mesylate salt thereof.

The compounds of the invention are believed to have utility in disorders wherein the inhibition of B-Raf activity is beneficial. The present invention thus provides for use in therapy, particularly in the treatment of disorders wherein the inhibition of B-Raf activity is beneficial, particularly cancer.

A further aspect of the invention provides a method of treatment of a disorder wherein inhibition of B-Raf activity is beneficial, comprising administering a combination of the invention.

A further aspect of the invention provides a method of treatment of a disorder associated with a BRAF V600E mutation wherein inhibition of B-Raf activity is beneficial, comprising administering the compounds of the invention.

A further aspect of the present invention provides the use of the compounds of the invention in the manufacture of a medicament for the treatment of a disorder wherein the inhibition of B-Raf activity is beneficial.

A further aspect of the present invention provides the use of compounds of the invention in the manufacture of a medicament for the treatment of a disorder associated with a BRAF V600E mutation wherein the inhibition of B-Raf activity is beneficial.

As used herein, "response to treatment" means a response to anti-cancer treatment may be measured in any way as is known and accepted in the art, including by following the response of the tumor (complete regression of the tumor(s) (complete response), reduction in size or volume of the tumor (s) (partial response); no apparent growth or progression of tumor(s) (stable disease), or mixed response (regression or stabilization of some tumors but not others)). Alternatively, the effect of anti-cancer treatment may be assessed by following the patient, e.g., by measuring and comparing survival time, or time to disease progression (disease-free survival). Any assessment of response may be compared to individuals who did not receive the treatment, or to individuals who received an alternative treatment.

The compounds of the invention are suitable for use in treatment of a cancer such that inhibition of B-Raf activity has a beneficial effect. "Susceptible cancers" include, but are limited to, both primary and metastatic forms of head and neck, breast cancer, inflammatory breast cancer, lung cancer, non-small cell lung cancer (NSCLC), colon cancer, prostate cancers, primary CNS tumors such as gliomas, glioblastomas, astrocytomas and ependymomas, and secondary CNS tumors (i.e., metastases to the central nervous system of tumors originating outside of the central nervous system), Bannayan-Zonana syndrome, Cowden disease, Lhermitte-Duclos disease, Wilm's tumor, Ewing's sarcoma, Rhabdomyosarcoma, ependymoma, medulloblastoma, colorectal cancer, renal cancer, kidney cancer, liver, melanoma, ovarian cancer, pancreatic, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia (AML), Chronic neutrophilic leukemia, plasmacytoma, Immunoblastic large cell leukemia, Mantle cell leukemia, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), Barret's adenocarcinoma; billiary tract carcinomas; cholangiocarcinoma; myelodysplastic syndromes, pituitary adenoma, and testicular cancer.

According to one embodiment, "susceptible cancer" refers to a cancer exhibiting a BRAF V600E mutation. The V600E amino acid substitution in B-Raf is described, for example, in Kumar et al. (2004) *J Invest Dermatol*. 122(2):342-8. This mutation commonly results from a T1799A mutation in the coding sequence for human B-Raf. Accordingly, in one embodiment of the present invention, the step of analyzing a sample from said neoplasm to determine whether a mutation encoding a V600E amino acid substitution is present in the coding sequence for B-Raf is performed by determining whether the coding sequence for B-Raf in cells of the neoplasm contains the T1799A mutation.

Suitably, the present invention relates to a method for treating or lessening the severity of melanoma. Suitably, the present invention relates to a method for treating or lessening the severity of V600E-mutant melanoma. Suitably, the present invention relates to a method for treating or lessening the severity of V600E-mutant metastatic melanoma.

Unless otherwise defined, in all dosing protocols described herein, the regimen of combined B-Raf inhibitor compound and immunotherapeutic does not have to commence at the start of treatment and terminate with the end of treatment. It is only required that at some point during treatment both the B-Raf inhibitor and the immunotherapeutic be administered on the same days.

As used herein the term "neoplasm" refers to an abnormal growth of cells or tissue and is understood to include benign, i.e., non-cancerous growths, and malignant, i.e., cancerous growths. The term "neoplastic" means of or related to a neoplasm.

As used herein the term "agent" is understood to mean a substance that produces a desired effect in a tissue, system, animal, mammal, human, or other subject. Accordingly, the term "anti-neoplastic agent" is understood to mean a substance producing an anti-neoplastic effect in a tissue, system, animal, mammal, human, or other subject. It is also to be understood that an "agent" may be a single compound, single antigen, or a combination or composition of two or more compounds or antigens.

By the term "treating" and derivatives thereof as used herein, is meant therapeutic therapy. In reference to a particular condition, treating means: (1) to ameliorate the condition or one or more of the biological manifestations of the condition, (2) to interfere with (a) one or more points in the biological cascade that leads to or is responsible for the condition or (b) one or more of the biological manifestations of the condition (3) to alleviate one or more of the symptoms, effects or side effects associated with the condition or one or more of the symptoms, effects or side effects associated with the condition or treatment thereof, or (4) to slow the progression of the condition or one or more of the biological manifestations of the condition.

As used herein, "prevention" is understood to refer to the prophylactic administration of a drug to substantially diminish the likelihood or severity of a condition or biological manifestation thereof, or to delay the onset of such condition or biological manifestation thereof. The skilled artisan will appreciate that "prevention" is not an absolute term. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The compounds of formula (I) and subformula thereof may be used in combination with other chemotherapeutics as described below. The compounds of formula (I) and subformula thereof and other chemotherapeutics may be employed in either concurrent or concomitant administration. Thus in one embodiment, one or more doses of compound of formula (I) or subformula thereof is administered simultaneously or separately with one or more doses of chemotherapeutic.

The term "loading dose" as used herein will be understood to mean a single dose or short duration regimen of compound of formula (I) or subformula thereof and/or the chemotherapeutic having a dosage higher than the maintenance dose administered to the subject to, for example, rapidly increase the blood concentration level of the drug. The term "maintenance dose" as used herein will be understood to mean a dose that is serially administered (for example; at least twice), and which is intended to either slowly raise blood concentration levels of the compound to a therapeutically effective level, or to maintain such a therapeutically effective level. The maintenance dose is generally administered once per day and the daily dose of the maintenance dose is lower than the total daily dose of the loading dose.

In one embodiment the mammal in the methods and uses of the present invention is a human.

Suitably, the present invention relates to a method of treating or lessening the severity of a cancer that is either wild type or mutant for each of Raf, Ras, MEK, and PI3K/Pten. This includes but is not limited to patients having cancers that are mutant for RAF, wild type for RAS, wild type for MEK, and wild type for PI3K/PTEN; mutant for RAF, mutant for RAS, wild type for MEK, and wild type for PI3K/PTEN; mutant for RAF, mutant for RAS, mutant for MEK, and wild type for PI3K/PTEN; and mutant for RAF, wild type for RAS, mutant for MEK, and wild type PI3K/PTEN.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Cancers that are either wild type or mutant for Raf, Ras, MEK, or mutant for PI3K/Pten are identified by known methods. For example, wild type or mutant tumor cells can be identified by DNA amplification and sequencing techniques, DNA and RNA detection techniques, including, but not limited to Northern and Southern blot, respectively, and/or various biochip and array technologies. Wild type and mutant polypeptides can be detected by a variety of techniques including, but not limited to immunodiagnostic techniques such as ELISA, Western blot or immunocyto chemistry. Suitably, Pyrophosphorolysis-activated polymerization (PAP) and/or PCR methods may be used. Liu, Q et al; Human Mutation 23:426-436 (2004).

As indicated, therapeutically effective amounts of Compound A is discussed above. The therapeutically effective amount of the further therapeutic agents of the present invention will depend upon a number of factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected in order to achieve the desired combined therapeutic effect.

In another aspect, the present invention provides pharmaceutical compositions comprising deuterated N-{3-[5-(2-Amino-4-pyrimidinyl)-2-(1,1-dimethylethyl)-1,3-thiazol-4-yl]-2-fluorophenyl}-2,6-difluorobenzenesulfonamide. Such pharmaceutical compositions may further comprise one or more other forms of N-{3-[5-(2-Amino-4-pyrimidinyl)-2-(1,1-dimethylethyl)-1,3-thiazol-4-yl]-2-fluorophenyl}-2,6-difluorobenzenesulfonamide and/or one or more pharmaceutically acceptable carriers or diluents. Examples of suitable pharmaceutical compositions and methods for their preparation are described in PCT Publication No. WO2009/137391, the subject matter of which is incorporated herein by reference in its entirety. Conveniently, suitable pharmaceutical compositions can be prepared using conventional techniques, and when employed, carriers and diluents. Pharmaceutical compositions for oral administration, such as tablet (and caplet) and capsule formulations, are preferred.

In the above-described methods of treatment and uses, a compound of the invention may be employed alone, in combination with one or more other compounds of the invention or in combination with other therapeutic methods or agents.

In particular, in methods of treating a condition attenuated by inhibition of at least one Raf family kinase and in methods of treating susceptible neoplasms, combination with other chemotherapeutic, biologic, hormonal, antibody and supportive care agents is envisaged as well as combination with surgical therapy and radiotherapy. Supportive care agents include analgesics, anti-emetics and agents used to treat heamatologic side effects such as neutropenia. Analgesics are well known in the art. Anti-emetics include but are not limited to $5HT_3$ antagonists such as ondansetron, granisetron, dolasetron, palonosetron and the like; prochlorperazine; metaclopromide; diphenhydramine; promethazine; dexamethasone; lorazepam; haloperidol; dronabinol; olanzapine; and neurokinin-1 antagonists such as aprepitant, fosaprepitant and casopitant administered alone or in various combinations.

The term "chemotherapeutic" as used herein refers to any chemical agent having a therapeutic effect on the subject to which it is administered. "Chemotherapeutic" agents include but are not limited to anti-neoplastic agents. As used herein, "anti-neoplastic agents" include both cytotoxic and cytostatic agents including biological, immunological and vaccine therapies. Combination therapies according to the invention thus comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent.

The compounds of the invention and at least one additional anti-neoplastic or supportive care therapy may be employed in combination concomitantly or sequentially in any therapeutically appropriate combination.

When a compound of the invention is used in combination with an anti-neoplastic and/or supportive care agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendant clinician.

Typical anti-neoplastic agents useful in the present invention include, but are not limited to: alkylating agents, antimetabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Examples of alkylating agents include but are not limited to nitrogen mustards such as cyclophosphamides, temozolamide, melphalan, and chlorambucil; oxazaphosphor-ines; alkyl sulfonates such as busulfan; nitrosoureas such as carmustine; triazenes such as dacarbazine; and platinum coordination complexes such as cisplatin, oxaliplatin and carboplatin.

Examples of antimetabolite anti-neoplastic agents include but are not limited to purine and pyrimidine analogues and anti-folate compounds, and more specifically, hydroxyurea, cytosine, arabinoside, ralitrexed, tegafur, fluorouracil (e.g., 5FU), methotrexate, cytarabine, mercaptopurine and thioguanine. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins. Examples of antimitotic agents include, but are not limited to, diterpenoids, vinca alkaloids, polo-like kinase (Plk) inhibitors and CenpE inhibitors. Examples of diterpenoids include, but are not limited to, paclitaxel and its analog docetaxel. Examples of vinca alkaloids include, but are not limited to, vinblastine, vincristine, vindesine and vinorelbine. Plk inhibitors are discussed further below. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the compounds of the invention in the compositions and methods described above. Examples of hormones and hormonal analogues believed to be useful in the treatment of neoplasms include, but are not limited to antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5α-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin. Examples of specific retinoids that may be used in combination with the compounds of the invention include: retinoic acid; all-trans-retinoic acid ("ATRA" also known as "tretinoin"); tamibarotene ("Am80"); 9-cis-retinoic acid ((2E,4E,6Z,8E)-3,7-Dimethyl-9-(2,6,6-trimethylcyclohex-1-enyl) nona-2,4,6,8-tetraenoic Acid) (also known as "9-cis-Tretinoin") (available from Sigma); Isotretinoin ((2Z,4E,6E, 8E)-3,7-dimethyl-9-(2,6,6-trimethyl-1-cyclohexenyl)nona-2,4,6,8-tetraenoic acid) (also known as "13-cis-retinoic acid") (ACUTANE®); Am580 (4-(5,6,7,8-tetrahydro-5,5,8,8-tetramethyl-2-naphtamido) benzoic acid), See, M. Gianni, *Blood* 1996 87(4):1520-1531; TTNPB (4-[E-2-(5,6,7,8-Tetrahydro-5,5,8,8-tetramethyl-2-naphthalenyl)-1-propenyl] benzoic acid) (also known as "Ro 13-7410") See, M. F. Boehm et al. *J. Med. Chem.* 1994 37:2930 and R. P. Bissonnette et al., *Mol. Cell. Biol.* 1995 15:5576; and BMS753 (4-[[(2,3-dihydro-1,1,3,3-tetramethyl-2-oxo-1H-inden-5-yl) carbonyl]amino]benzoic acid) See, U.S. Pat. No. 6,184,256. Other RARα agonists known the art may also be used in the present invention.

Receptor tyrosine kinase inhibitors which may be combined with the compounds of the invention include those involved in the regulation of cell growth, which receptor tyrosine kinases are sometimes referred to as "growth factor receptors." Examples of growth factor receptor inhibitors, include but are not limited to inhibitors of: insulin growth factor receptors (IGF-1R, IR and IRR); epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-fms), c-kit, c-met, fibroblast growth factor receptors (FGFRs), hepatocyte growth factor receptors (HGFRs), Trk receptors (TrkA, TrkB, and TrkC), ephrin (Eph) receptors and the RET protooncogene.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib (GLEEVEC®) is one example of a PDGFR inhibitor. Examples of VEGFR inhibitors include pazopanib, ZD6474, AZD2171, PTK787, sunitinib and sorafenib.

Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, Abl kinase (c-Abl and Bcr-Abl), FAK (focal adhesion kinase) and Bruton's tyrosine kinase (BTK). Non-receptor kinases and agents, which inhibit non-receptor tyrosine kinase function, are described in Sinha, S, and Corey, S. J., (1999) *J. Hematother. Stem Cell Res.* 8:465-80; and Bolen, J. B. and Brugge, J. S., (1997) *Annu. Rev. of Immunol.* 15:371-404. SH2/SH3 domain blockers are agents that disrupt SH2 or SH3 domain binding in a variety of enzymes or adaptor proteins including, but not limited to, PI3-K p85 subunit, Src family kinases, adaptor molecules (Shc, Crk, Nck, Grb2) and Ras-GAP. Examples of Src inhibitors include, but are not limited to, dasatinib and BMS-354825 (J. Med. Chem (2004) 47:6658-6661).

Inhibitors of serine/threonine kinases may also be used in combination with the compounds of the invention in any of the compositions and methods described above. Examples of serine/threonine kinase inhibitors that may also be used in combination with a compound of the present invention include, but are not limited to, polo-like kinase inhibitors (Plk family e.g., Plk1, Plk2, and Plk3), which play critical roles in regulating processes in the cell cycle including the entry into and the exit from mitosis; MAP kinase cascade blockers, which include other Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers, including inhibitors of PKC subtypes (alpha, beta, gamma, epsilon, mu, lambda, iota, zeta); inhibitors of kappa-B (IkB) kinase family (IKK-alpha, IKK-beta); PKB/Akt kinase family inhibitors; and inhibitors of TGF-beta receptor kinases. Examples of Plk inhibitors are described in PCT Publication No. WO04/014899 and WO07/03036. Other examples of serine/threonine kinase inhibitors are known in the art. In another embodiment, the present invention provides methods of treatment of any of the various conditions enumerated above comprising administering a compound of the invention in combination with a Plk inhibitor. In one particular embodiment, the methods of the present invention comprise administering a compound of the invention in combination with 5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide.

Inhibitors of Ras oncogene may also be useful in combination with the compounds of the present invention. Such inhibitors include, but are not limited to, inhibitors of farnesyltransferase, geranyl-geranyl transferase, and CAAX proteases as well as anti-sense oligonucleotides, ribozymes and immunotherapy. Such inhibitors have been shown to block Ras activation in cells containing mutant Ras, thereby acting as antiproliferative agents.

Inhibitors of kinases involved in the IGF-1R signaling axis may also be useful in combination with the compounds of the present invention. Such inhibitors include but are not limited to inhibitors of JNK1/2/3, PI3K, AKT and MEK, and 14.3.3 signaling inhibitors. Examples of AKT inhibitors are described in PCT Publication No. WO 2007/058850, published 24 May 2007 which corresponds to PCT Application No. PCT/US2006/043513, filed 9 Nov. 2006. One particular AKT inhibitor disclosed therein is 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol.

Additional combination chemotherapeutics include cell cycle signaling inhibitors, including inhibitors of cyclin dependent kinases (CDKs) including CDK2, CDK4, and CDK6 and inhibitors for the same (see Rosania G. R., et al., *Exp. Opin. Ther. Patents* (2000) 10:215-230), anti-VEGF antibodies, such as bevacizumab (AVASTIN®), which do not recognize VEGFR (the receptor tyrosine kinase), but bind to the ligand; small molecule inhibitors of integrin (alpha$_v$, beta$_3$) that inhibit angiogenesis; endostatin and angiostatin (non-RTK), inhibitors of phosphatidyl inositol-3-OH kinase family members including blockers of PI3-kinase, ATM, DNA-PK, and Ku, and inhibitors of mTOR, including inhibitors of TORC1 and/or TORC2.

Additional combination chemotherapeutics include myo-inositol signaling inhibitors, such as phospholipase C blockers and myoinositol analogues, siRNA, RNAi, locked nucleic acid polynucleotides, and Bcl-2 antisense oligonucleotides, namely Genta's G3139 bcl-2 antisense oligonucleotide (see Water, J. S., et al., *J. Clin. Oncol.* (2000) 18:1812-1823; and Kitada, S., et al., *Antisense Res. Dev.* (1994) 4:71-79).

EXAMPLES

The following examples are intended for illustration only and are not intended to limit the scope of the invention in any way.

Example 1

Preparation of deuterated N-{3-[5-(2-Amino-4-pyrimidinyl)-2-(1,1-dimethylethyl)-1,3-thiazol-4-yl]-2-fluorophenyl}-2,6-difluorobenzenesulfonamide

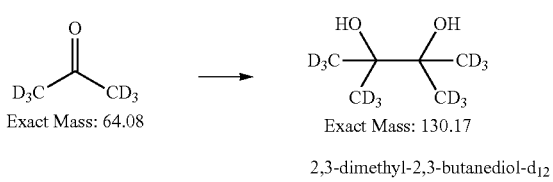

2,3-dimethyl-2,3-butanediol-d$_{12}$

A mixture of magnesium (10 g, 411 mmol) and benzene (100 mL) was stirred at room temperature (rt) for 10 minutes, and then a solution of mercury(II) chloride (11.25 g, 41.4 mmol) in acetone-d$_6$(40 mL) was added over 20 minutes. The reaction mixture was warmed to 50° C. for 20 minutes. Acetone-d$_6$ (60 mL) was added over 20 minutes to the reaction mixture, after addition the reaction mixture was stirred at 50° C. for 30 minutes and then refluxed for 1 hour. The reaction mixture was cooled to rt and water (25 mL) was added. The reaction mixture was refluxed for an additional 1 hour, then cooled and filtered. The residual cake was refluxed with benzene (100 mL) for 10 minutes and filtered. The combined filtrates were evaporated under decreased pressure to afford the crude product. Water (40 mL) was added to the crude product and was cooled to 0° C. over 1 hour. The resulting solids were filtered and washed with toluene (50 mL), dried under vacuum to afford the desired 2,3-dimethyl-2,3-butanediol-d$_{12}$ (38 g, 291 mmol, 21% yield) as a white solid.

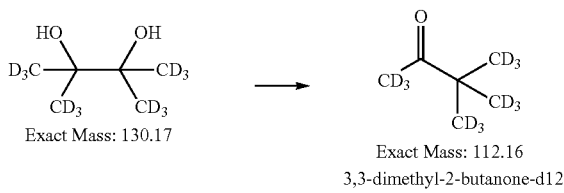 [SMILES: [2H]C([2H])([2H])C(O)(C([2H])([2H])[2H])C(O)(C([2H])([2H])[2H])C([2H])([2H])[2H] ; [2H]C([2H])([2H])C(=O)C(C([2H])([2H])[2H])(C([2H])([2H])[2H])C([2H])([2H])[2H]]

To a 500 mL flask was added 2,3-dimethyl-2,3-butanediol-d$_{12}$ (38 g, 256 mmol), deuterium oxide (40 mL, 2211 mmol) and sulfuric acid-d$_2$ (15 mL, 256 mmol). The reaction flask was equipped with distillation equipment and then gradually heated to 120° C. in an oil bath. The fraction boiling from 70° C. to 100° C. was collected and decanted. The upper layer was separated and dried to afford 3,3-dimethyl-2-butanone-d$_{12}$ (16 g, 14.2 mmol, 48.9% yield).

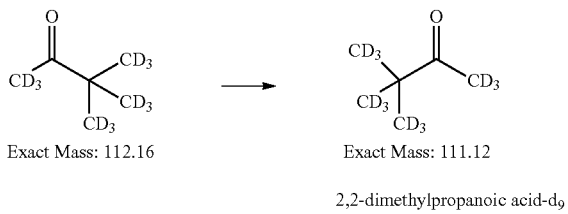 [SMILES: [2H]C([2H])([2H])C(=O)C(C([2H])([2H])[2H])(C([2H])([2H])[2H])C([2H])([2H])[2H] ; [2H]C([2H])([2H])C(=O)C(C([2H])([2H])[2H])(C([2H])([2H])[2H])C([2H])([2H])[2H]]

2,2-dimethylpropanoic acid-d$_9$

Sodium hydroxide (45.6 g, 1140 mmol) was dissolved in water (400 mL) and cooled to 0° C. Bromine (22.03 mL, 428 mmol) was added over 30 minutes. After addition completed, the reaction mixture was stirred at 0° C. for 10 minutes. 3,3-Dimethyl-2-butanone-d$_{12}$ (16 g, 143 mmol) was added over 10 minutes, the mixture was stirred at 0° C. for 4 hours and then warmed to rt overnight. The reaction mixture was evaporated under decreased pressure to remove half of water. The undistilled solution was cooled to rt and filtered. The filtrate was acidified with conc. H$_2$SO$_4$ and distilled under normal pressure, about 100 mL of distillate was collected and extracted with ether (50 mL×3). The combined organic layers were dried (Na$_2$SO$_4$) and evaporated to afford the crude 2,2-dimethylpropanoic acid-d$_9$ (11.7 g, 105 mmol, 73% yield) as yellow oil. LCMS m/z=110, 111.

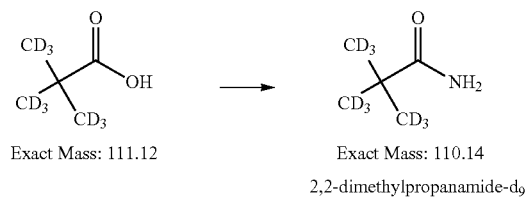

2,2-dimethylpropanamide-d$_9$

A solution of 2,2-dimethylpropanoic acid-d$_9$ (20 g, 180 mmol) in dichloromethane (DCM) (150 mL) and DMF (10 drops) was cooled to 0° C. Oxalyl chloride (15.75 mL, 180 mmol) was added dropwise. After addition, the reaction mixture was stirred at rt until gas elution stopped. The reaction mixture was added dropwise to the NH$_3$ solution in dioxane (1079 mL, 540 mmol), after addition the resulting suspension was stirred at rt overnight. The reaction mixture was evaporated under decreased pressure. The resulting white solid was added DCM (150 mL) and stirred at rt for 1 hour. The reaction mixture was filtered. The residual cake was washed with DCM (100 mL×2) and filtered. The combined filtrates were dried (Na$_2$SO$_4$) and evaporated under decreased pressure to afford the desired 2,2-dimethylpropanamide-d$_9$ (19.5 g, 168 mmol, 93% yield) as a white solid. LCMS: m/z=111 (M+1).

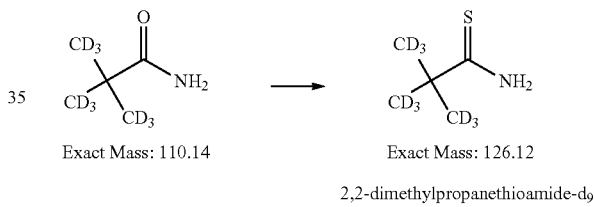

2,2-dimethylpropanethioamide-d$_9$

A solution of 2,2-dimethylpropanamide-d$_9$ (6.61 g, 60 mmol) and Lawesson's reagent (12.13 g, 30.0 mmol) in tetrahydrofuran (THF) (100 mL) was heated to reflux overnight. LCMS showed full conversion of starting material. The mixture was cooled to rt and poured into saturated aqueous NaHCO$_3$ (300 mL). The mixture was extracted with ether (100 mL×4), the combined organic layers were dried over Na$_2$SO$_4$ and evaporated to leave the crude product, which was purified by chromatography (SiO$_2$ 300-400 mesh, EtOAc:PE, 1:4) to afford the desired 2,2-dimethylpropanethioamide-d$_9$ (2.64 g, 20.70 mmol, 34.5% yield) as white solid. LCMS m/z=127.2 (M+1).

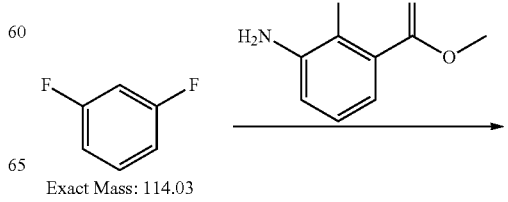

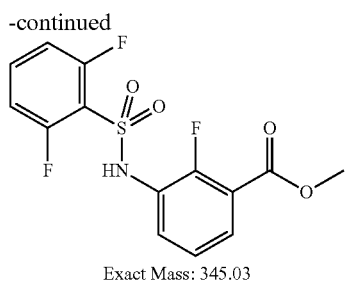

Exact Mass: 345.03
3-(2,6-difluorophenylsulfonamido)-2-fluorobenzoate

To a cooled solution of 1,3-difluorobenzene (9.4 g, 82 mmol) in diethyl ether (120 mL) was added n-BuLi in hexane (32.3 mL, 81 mmol) dropwise at −78° C. The reaction mixture was stirred at −78° C. for 3 h. Sulfur dioxide (106 g, 1648 mmol) was flushed into the solution and stirred at −60° C. for 20 mins, which produced a white solid. NCS (12.10 g, 91 mmol) was added and the reaction mixture was warmed to rt and for 1 h. The reaction mixture with white solid changed to pale brown solution. The reaction mixture was filtered and concentrated to give crude 2,6-difluorobenzenesulfonyl chloride, which was added dropwise into methyl 3-amino-2-fluorobenzoate (5.19 g, 30.7 mmol) in pyridine (50 mL) at 15° C. After the addition, the reaction mixture was stirred at room temperature overnight. Ethyl acetate (100 mL) was added to the reaction mixture and then followed by 40 mL of cold water. The mixture was heated to 55° C. with stirring until all red solids dissolved. The upper layer was organic layer which was isolated and washed again with water. The organic layer was dried and evaporated under reduced pressure. Petro ether was added to the crude product and heated to reflux and then cooled to 5° C. The solids were filtered and rinsed with petro ether to afford methyl 3-(2,6-difluorophenylsulfonamido)-2-fluorobenzoate (6.91 g, 10.35 mmol, 12.56% yield) as orange solid. LCMS: $[M+NH_4]^+$=363.0.

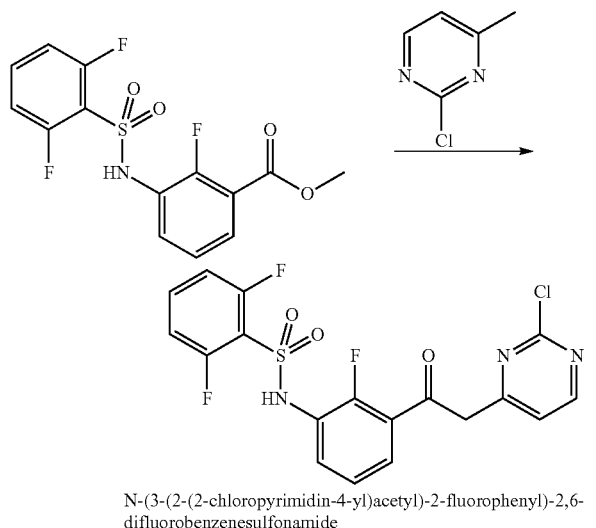

N-(3-(2-(2-chloropyrimidin-4-yl)acetyl)-2-fluorophenyl)-2,6-difluorobenzenesulfonamide To a solution of methyl 3-(2,6-difluorophenylsulfonamido)-2-fluorobenzoate (6.6 g, 19.11 mmol) in tetrahydrofuran (THF) (80 mL) stirred under nitrogen at −30° C. was added the solution of LiHMDS (65 mL, 65 mmol) in tetrahydrofuran dropwise over 40 mins. The reaction mixture was stirred at −5° C. for 2 hours. The reaction mixture was cooled again to −30° C. 2-Chloro-4-methylpyrimidine (2.95 g, 22.94 mmol) in tetrahydrofuran (THF) (10 mL) was added dropwise to the reaction mixture. The reaction mixture was stirred at −10° C. for 1 h, and warmed to room temperature for another 1.5 hours. The reaction mixture was cooled to 0° C. and quenched by addition of the satureated aqueous $NH_4Cl$ (80 mL) and extracted with ethyl acetate (100 ml×3). The combined organic layers were washed with water and brine, dried over $Na_2SO_4$, filtered and concentrated under reduced pressure to afford the crude product, which was purified by silica gel chromatography with petroleum ether/EtOAc (2:1) to produce the N-(3-(2-(2-chloropyrimidin-4-yl)acetyl)-2-fluorophenyl)-2,6-difluorobenzenesulfonamide (5.05 g, 6.37 mmol, 33.3% yield). LCMS $[M+H]^+$=442.

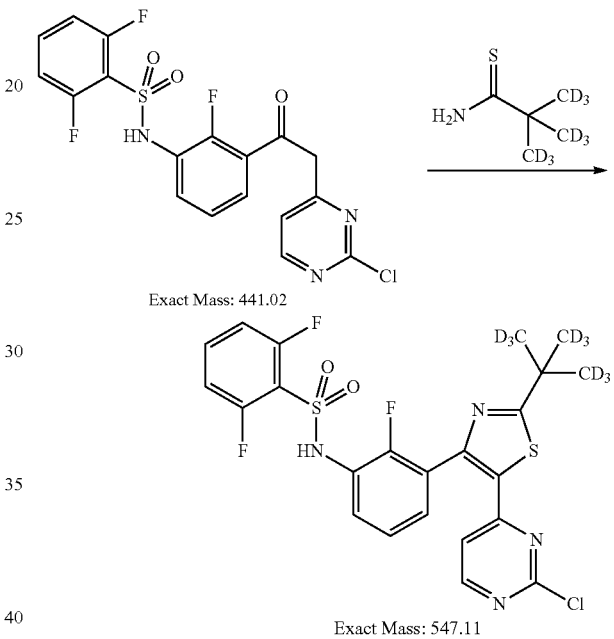

Exact Mass: 441.02

Exact Mass: 547.11

General procedure for synthesis of N-(3-(2-tert-butyl-5-(2-chloropyrimidin-4-yl)thiazol-4-yl)-2-fluorophenyl)-2,6-difluorobenzenesulfonamide-d$_9$ N-(3-(2-(2-Chloropyrimidin-4-yl)acetyl)-2-fluorophenyl)-2,6-difluorobenzenesulfonamide (8.65 g, 19.58 mmol) was stirred in N,N-dimethylacetamide (DMA) (80 ml) followed by addition of the NBS (3.48 g, 19.58 mmol) in three portions over 30 mins at room temperature. The reaction mixture was stirred for 2.5 h, then 2,2-dimethylpropanethioamide-d$_9$ (2.472 g, 19.58 mmol) was added to the reaction mixture solution. The reaction mixture was warmed to 65° C. with stirring overnight (12 h). The reaction mixture was cooled and diluted with water (200 mL) and extracted with EtOAc (200 mL×3), and dried over $Na_2SO_4$ and concentrated to dryness to afford crude N-(3-(2-tert-butyl-5-(2-chloropyrimidin-4-yl)thiazol-4-yl)-2-fluorophenyl)-2,6-difluorobenzenesulfonamide-d$_9$.

General Purification Procedure

The multiple batches of crude N-(3-(2-tert-butyl-5-(2-chloropyrimidin-4-yl)thiazol-4-yl)-2-fluorophenyl)-2,6-difluorobenzenesulfonamide-d$_9$ were purified by silica gel chromatography with petroleum ether/EtOAc (4:1) to afford N-(3-(2-tert-butyl-5-(2-chloropyrimidin-4-yl)thiazol-4-yl)-

2-fluorophenyl)-2,6-difluorobenzenesulfonamide-d₉ (6.23 g, 10.12 mmol) as a white solid. LCMS m/z=547[M]⁺.

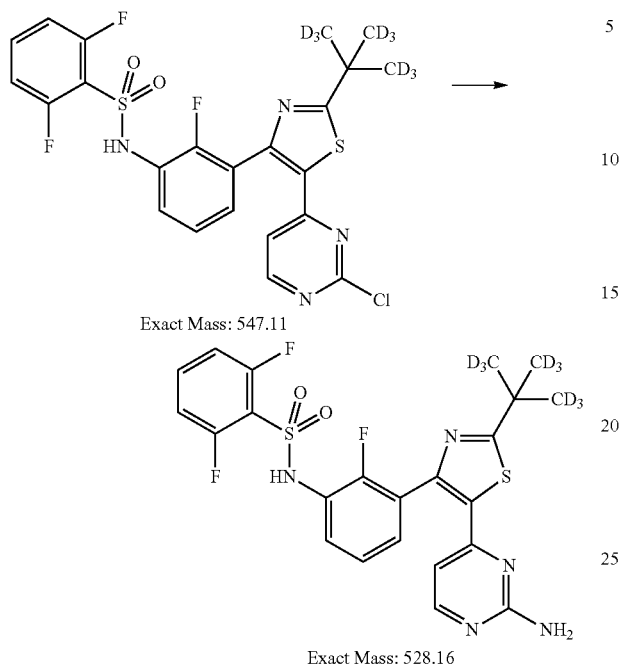

General procedure for synthesis of N-(3-(5-(2-aminopyrimidin-4-yl)-2-tert-butylthiazol-4-yl)-2-fluorophenyl)-2,6-difluorobenzenesulfonamide-d₉

N-(3-(2-tert-butyl-5-(2-chloropyrimidin-4-yl)thiazol-4-yl)-2-fluorophenyl)-2,6-difluorobenzenesulfonamide-d₉ (610 mg, 1.113 mmol) in conc. ammonium hydroxide (5.5 mL, 36.7 mmol) solution was stirred at 100° C. in sealed tube for 4 h. The solvent was removed under reduced pressure. Water and ethyl acetate (100 mL/150 mL) were added to the mixture, and extracted with ethyl acetate (100 mL×2). The combined organic layers were dried over with Na₂SO₄. The solvent was removed under pressure to produce the crude N-(3-(5-(2-aminopyrimidin-4-yl)-2-tert-butylthiazol-4-yl)-2-fluorophenyl)-2,6-difluorobenzenesulfonamide-d₉.

General Purification Procedure

The multiple batches of crude N-(3-(5-(2-aminopyrimidin-4-yl)-2-tert-butylthiazol-4-yl)-2-fluorophenyl)-2,6-difluorobenzenesulfonamide-d₉ were purified by silica gel chromatography with petroleum ether/EtOAc (2:1) to produce N-(3-(5-(2-aminopyrimidin-4-yl)-2-tert-butylthiazol-4-yl)-2-fluorophenyl)-2,6-difluorobenzenesulfonamide-d₉ (3.34 g, 6.18 mmol) as white solid. The solids were washed with ethyl ether and a small amount of DCM to afford N-(3-(5-(2-aminopyrimidin-4-yl)-2-tert-butylthiazol-4-yl)-2-fluorophenyl)-2,6-difluorobenzenesulfonamide-d₉. LCMS [M+H]⁺ =529; ¹H NMR (400 MHz, DMSO) δ10.86 (s, 1H), 7.97 (d, J=4.8 Hz, 1H), 7.69 (t, 1H), 7.46-7.24 (m, 5H), 6.75 (s, 2H), 5.84 (d, J=5.2, 1H).

The invention claimed is:
1. A compound having Formula (Ic):

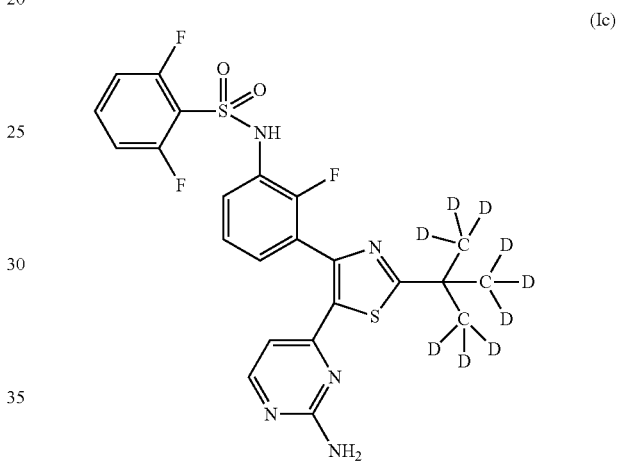

wherein
"-D" represents a deuterium atom, and
any atom not designated as deuterium is present at its natural isotopic abundance.

* * * * *